(12) United States Patent
Brandl

(10) Patent No.: US 10,631,831 B2
(45) Date of Patent: Apr. 28, 2020

(54) METHODS AND SYSTEMS FOR ADJUSTING A FIELD OF VIEW FOR MEDICAL IMAGING SYSTEMS

(71) Applicant: General Electric Company, Schenectady, NY (US)

(72) Inventor: Helmut Brandl, Zipf (AT)

(73) Assignee: General Electric Company, Schenectady, NY (US)

( * ) Notice: Subject to any disclaimer, the term of this patent is extended or adjusted under 35 U.S.C. 154(b) by 855 days.

(21) Appl. No.: 15/274,634

(22) Filed: Sep. 23, 2016

(65) Prior Publication Data

US 2018/0085096 A1  Mar. 29, 2018

(51) Int. Cl.
*A61B 8/00* (2006.01)
*A61B 8/08* (2006.01)

(52) U.S. Cl.
CPC ............... *A61B 8/54* (2013.01); *A61B 8/469* (2013.01); *A61B 8/5207* (2013.01); *A61B 8/4494* (2013.01); *A61B 8/463* (2013.01); *A61B 8/465* (2013.01); *A61B 8/488* (2013.01)

(58) Field of Classification Search
CPC .......... A61B 8/54; A61B 8/465; A61B 8/463; A61B 8/5207; A61B 8/469; A61B 8/4494; A61B 8/488
See application file for complete search history.

(56) References Cited

U.S. PATENT DOCUMENTS

| | | | | |
|---|---|---|---|---|
| 5,487,388 A * | 1/1996 | Rello | ................ | A61B 8/08 128/916 |
| 8,137,278 B2 * | 3/2012 | Lundberg | ................ | A61B 8/08 600/443 |
| 10,345,444 B2 * | 7/2019 | Olsson | ................ | G01S 15/8995 |
| 2003/0236461 A1 * | 12/2003 | Poland | ................ | G01N 29/0609 600/443 |
| 2012/0071761 A1 * | 3/2012 | Miller | ................ | B06B 1/0625 600/459 |
| 2012/0071763 A1 * | 3/2012 | Miller | ................ | B06B 1/0625 600/459 |
| 2012/0095343 A1 * | 4/2012 | Smith | ................ | A61B 8/58 600/447 |
| 2012/0243367 A1 * | 9/2012 | Hwang | ................ | A61B 8/00 367/7 |
| 2013/0012819 A1 | 1/2013 | Haugen et al. | | |
| 2013/0231569 A1 * | 9/2013 | Miller | ................ | B06B 1/0625 600/459 |
| 2018/0125460 A1 * | 5/2018 | Perrey | ................ | A61B 8/13 |

\* cited by examiner

*Primary Examiner* — Angela M Hoffa
(74) *Attorney, Agent, or Firm* — The Small Patent Law Group LLC; Dean D. Small

(57) ABSTRACT

Systems and methods are provided for adjusting a field of view of a medical imaging system, such as for an ultrasound imaging system. A system (e.g., an ultrasound imaging system) is provided herein that includes a matrix array probe. The matrix array probe includes a plurality of transducer elements arranged in an array with an elevation direction and an azimuth direction. The system includes a controller circuit that is configured to control the matrix array probe to acquire ultrasound data from a sector field of view (FOV) with a subset of the plurality of transducer elements. The sector FOV having a virtual apex. The controller circuit is further configured to shift the virtual apex and the corresponding sector FOV from a first sector FOV that has at least one ultrasound obstructed region to a second sector FOV that encompasses the ultrasound obstructed region.

20 Claims, 10 Drawing Sheets

METHODS AND SYSTEMS FOR ADJUSTING A FIELD OF VIEW FOR MEDICAL IMAGING SYSTEMS

FIELD

Embodiments described herein generally relate to methods and systems for adjusting a field of view of a medical imaging system, such as for an ultrasound imaging system, for diagnostic medical imaging.

BACKGROUND OF THE INVENTION

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound systems are controllable to operate in different modes of operation to perform the different scans. The signals received at the probe are then communicated and processed at a back end.

Conventional ultrasound probes generate ultrasound signals to a body of interest defining a field of view (FOV) of the conventional ultrasound probe. The FOV extends along an image angle centered at a static apex. A position of the static apex is centered within the conventional ultrasound probe such that the FOV of the conventional ultrasound probe is symmetric with respect to the conventional ultrasound probe. During a scan of the body of interest, ultrasound obstructions such as anatomical structures (e.g., bones), fluids, air, and/or the like can be interposed between the conventional ultrasound probes and the body of interest obstructing an ultrasound image. Due to the symmetric position of the FOV and the static apex, the clinician must adjust a position of the conventional ultrasound probe with respect to the body of interest. Alternatively, the clinician must perform a secondary scan utilizing an alternative conventional ultrasound probe.

BRIEF DESCRIPTION OF THE INVENTION

In an embodiment a system (e.g., an ultrasound imaging system) is provided. The system includes a matrix array probe. The matrix array probe includes a plurality of transducer elements arranged in an array with an elevation direction and an azimuth direction. The system includes a controller circuit that is configured to control the matrix array probe to acquire ultrasound data from a sector field of view (FOV) with a subset of the plurality of transducer elements. The sector FOV having a virtual apex. The controller circuit is further configured to shift the virtual apex and the corresponding sector FOV from a first sector FOV that has at least one ultrasound obstructed region to a second sector FOV that encompasses the ultrasound obstructed region.

In an embodiment a method (e.g., for adjusting a sector field of view (FOV) of a matrix array probe) is provided. The method includes acquiring ultrasound data from a sector FOV with a subset of a plurality of transducer elements of a matrix array probe. The plurality of transducer elements are arranged in an array with an elevation direction and an azimuth direction, the sector FOV having a virtual apex. The method includes shifting the virtual apex and the corresponding sector FOV.

In an embodiment a system (e.g., an ultrasound imaging system) is provided. The system includes a matrix array probe that includes a plurality of transducer elements arranged in an array with an elevation direction and an azimuth direction. The plurality of transducer elements form a curved surface area of the matrix array probe. The system includes a controller circuit that is configured to control the matrix array probe to acquire ultrasound data from a sector field of view (FOV) with a subset of the plurality of transducer elements. The sector FOV having a virtual apex. The controller circuit is further configured to shift the virtual apex and the corresponding sector FOV.

DETAILED DESCRIPTION OF THE INVENTION

Figure 1:
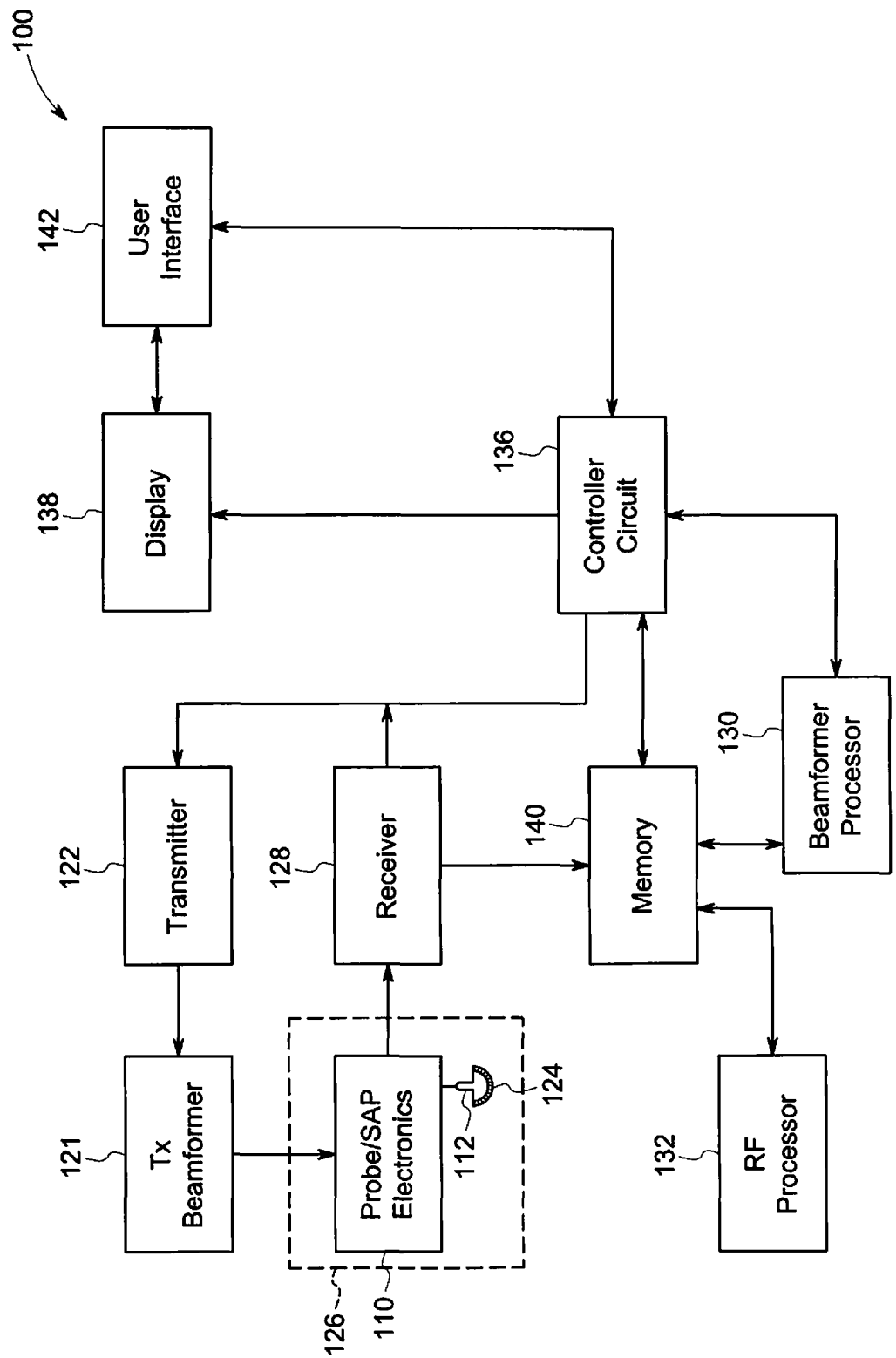
FIG. 1 illustrates a schematic block diagram of an ultrasound imaging system, in accordance with an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for a steerable field of view (FOV) of an ultrasound transducer (e.g., ultrasound probe). The ultrasound probe includes a matrix array of a plurality of transducer elements. The matrix array may form a curved array having an elevation direction and an azimuth direction. The ultrasound probe may be communicatively coupled to a controller circuit. The controller circuit may be configured to control the ultrasound transducer to acquire ultrasound data. In various embodiments, the controller circuit may be configured to allow for keyhole scanning of the transducer array by producing a wide sector image out of a small coupling area. For example, the controller circuit may utilize asymmetrical beam-steering to adjust a virtual apex of a sector FOV of the ultrasound probe to include a region of interest. The controller circuit may adjust the virtual apex based on one or signals received from user interface components. For example, the ultrasound t probe may include a user interface component (e.g., a rotary button) for setting an image angle. In another example, a touchscreen communicatively coupled to the controller circuit. The touchscreen may include one or more user interface component (e.g., a pair of +/− buttons, left/right buttons,) shown on a graphical user interface to adjust a wide sector angle, steer the sector FOV, and/or the like. In another example, a dedicated user interface (e.g., trackball, keyboard, mouse, and/or the like) is communicatively coupled to the controller circuit to adjust the wide sector angle, steer the sector FOV, and/or the like.

FIG. 1 is a schematic diagram of a diagnostic medical imaging system, specifically, an ultrasound imaging system 100. The ultrasound imaging system 100 includes an ultrasound probe 126 having a transmitter 122, transmit beamformer 121 and probe/SAP electronics 110. The probe/SAP electronics 110 may be used to control the switching of the transducer elements 124. The probe/SAP electronics 110 may also be used to group transducer elements 124 into one or more sub-apertures.

The ultrasound probe 126 may be configured to acquire ultrasound data or information from a region of interest (e.g., organ, blood vessel, heart) of the patient. The ultrasound probe 126 is communicatively coupled to the controller circuit 136 via the transmitter 122. The transmitter 122 transmits a signal to a transmit beamformer 121 based on acquisition settings received by the controller circuit 136. The acquisition settings may define an amplitude, pulse width, frequency, and/or the like of the ultrasonic pulses emitted by the transducer elements 124. The transducer elements 124 emit pulsed ultrasonic signals into a patient (e.g., a body). The acquisition settings may be adjusted by the user by selecting a gain setting, power, time gain compensation (TGC), resolution, and/or the like from the user interface 142. The signal transmitted by the transmitter 122 in turn drives a plurality of transducer elements 124 within a transducer array 112. In connection with FIGS. 2A-B, the transducer array 112 may be a matrix array of transducer elements 124 arranged to include an elevation direction and an azimuth direction. For example only, the transducer array 112 may include an array of 128 transducer elements 124 along the azimuth plane 206 by 64 transducer elements 124 along the elevation plane 208 to from a matrix array probe (e.g., the ultrasound probe 126). It may be noted that in various other embodiments a number of transducer elements 124 along the azimuth and elevation plane 206, 208 may be more and/or less than the above described embodiment.

Figure 2A:
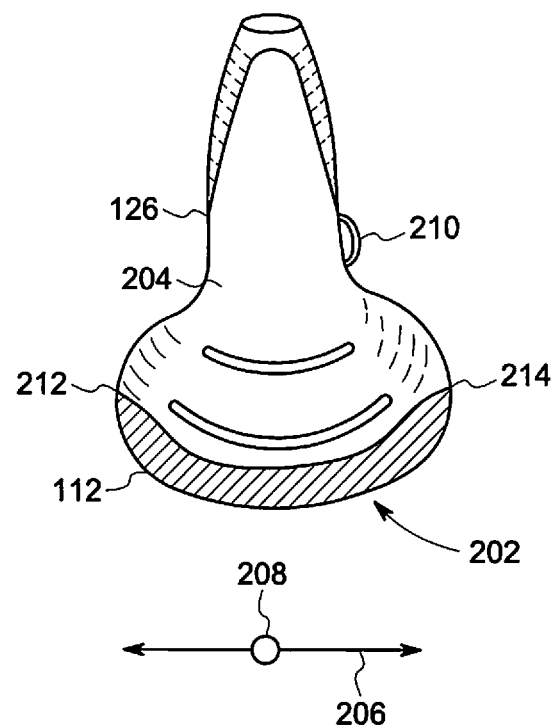
FIG. 2A illustrates an ultrasound probe of an embodiment along an azimuth plane of the ultrasound imaging system shown in FIG. 1.

FIG. 2A illustrates the ultrasound probe 126 of an embodiment along an azimuth plane 206. The ultrasound probe 126 includes a housing 204 configured to enclose the probe/SAP electronics 110 and affix the transducer array 112 to a front end 202 of the ultrasound probe 126. The housing 204 may include one or more user interface components 210, such as a tactile button, rotary button, capacitive button, and/or the like. The front end 202 of the housing 204 shown in FIG. 2A is configured to hold and/or confine the transducer array 112, which is shown extending along the azimuth plane 206, to the housing 202. The azimuth plane 206 is shown as a standard plane extending along a length of the ultrasound probe 126. It may be noted a variety of a geometries and/or configurations may be used for the transducer array 112. For example, the transducer elements 124 of the transducer array 112 forms a curved surface area of the ultrasound probe 126 such that opposing ends 212, 214 of the transducer array 112 deviates from a center portion of the transducer array 112.

Figure 2B:
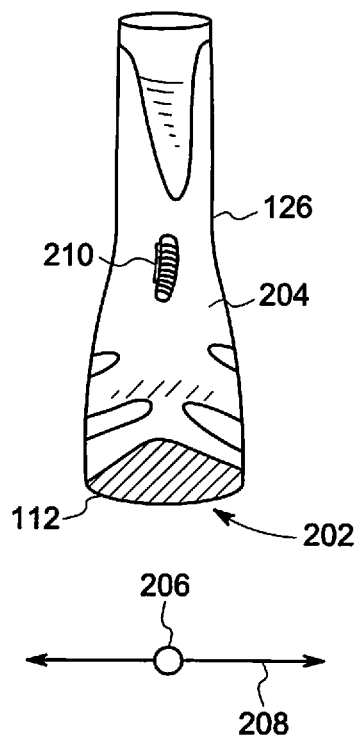
FIG. 2B illustrates an ultrasound probe of an embodiment along an elevation plane of the ultrasound imaging system shown in FIG. 1.

FIG. 2B illustrates the ultrasound probe 126 of an embodiment along an elevation plane 208. The elevation plane 208 is orthogonal to the azimuth plane 206. For example, the ultrasound probe 126 shown in FIG. 2B is a side view relative to the ultrasound probe 126 of FIG. 2A.

Returning to FIG. 1, the transducer elements 124 emit pulsed ultrasonic signals into a body (e.g., patient) or volume corresponding to the acquisition settings along one or more scan planes. The ultrasonic signals may include, for example, one or more reference pulses, one or more pushing pulses (e.g., shear-waves), and/or one or more pulsed wave Doppler pulses. At least a portion of the pulsed ultrasonic signals back-scatter from a region of interest (ROI) (e.g., heart, left ventricular outflow tract, breast tissues, liver tissues, cardiac tissues, prostate tissues, neonatal brain, embryo, abdomen, and the like) to produce echoes. The echoes are delayed in time and/or frequency according to a depth or movement, and are received by the transducer elements 124 within the transducer array 112. The ultrasonic signals may be used for imaging, for generating and/or tracking shear-waves, for measuring changes in position or velocity within the ROI (e.g., flow velocity, movement of blood cells), differences in compression displacement of the tissue (e.g., strain), and/or for therapy, among other uses. For example, the probe 126 may deliver low energy pulses during imaging and tracking, medium to high energy pulses to generate shear-waves, and high energy pulses during therapy.

The transducer elements 124 convert the received echo signals into electrical signals which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored on memory 140, temporarily. The digitized signals correspond to the backscattered waves receives by each transducer element 124 at various times. After digitization, the signals still may preserve the amplitude, frequency, phase information of the backscatter waves.

Optionally, the controller circuit 136 may retrieve the digitized signals stored in the memory 140 to prepare for the beamformer processor 130. For example, the controller circuit 136 may convert the digitized signals to baseband signals or compressing the digitized signals.

The beamformer processor 130 may include one or more processors. Optionally, the beamformer processor 130 may include a central controller circuit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 140) for beamforming calculations using any suitable beamforming method such as adaptive beamforming, synthetic transmit focus, aberration correction, synthetic aperture, clutter reduction and/or adaptive noise control, and/or the like. Optionally, the beamformer processor 130 may be integrated with and/or apart of the controller circuit 136. For example, the operations described being performed by the beamformer processor 130 may be configured to be performed by the controller circuit 136.

Figure 3:
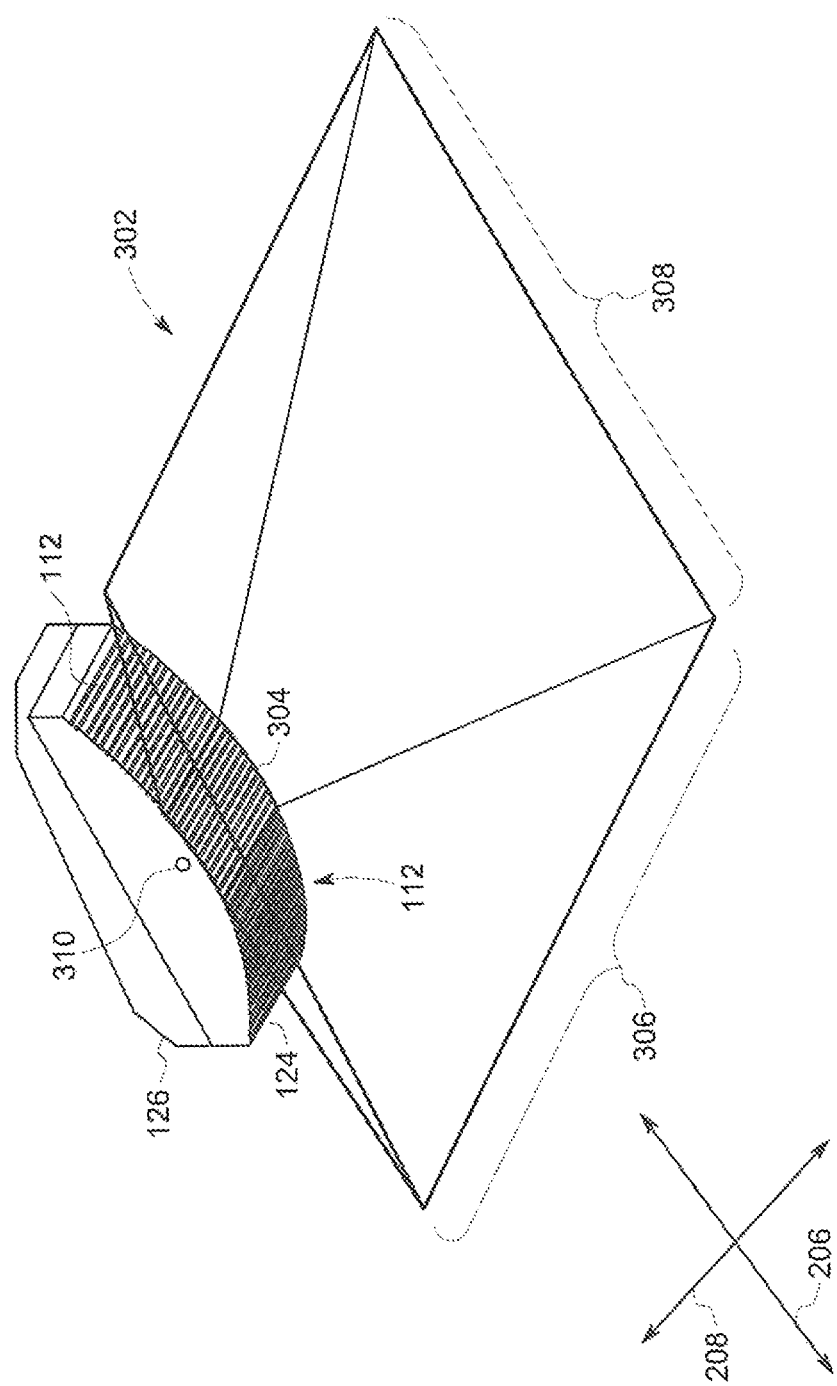
FIG. 3 illustrates a sector field of view of an embodiment of the ultrasound probe.

In connection with FIG. 3, the controller circuit 136 may be configured to define a sector FOV 302 based on a subset of the plurality of transducer elements as an active footprint 304 of the transducer array 112, which is utilized by the beamformer processor 130.

FIG. 3 illustrates the sector FOV 302 of an embodiment of the ultrasound probe 126. The sector FOV 302 may define an area and/or volume extending from the transducer array 112 the ultrasound imaging system 100 acquires ultrasound data. The sector FOV 302 includes a virtual apex 310. A position of the virtual apex 310 may be defined by the controller circuit 136 based on a selection of inputs from the user interface component 210 and/or a user interface 142. For example, the controller circuit 136 may be configured to adjust the sector FOV 302 based on a selection of the one or more user interface components 210 and/or the user interface 142. Additionally or alternatively, the controller circuit 136 may define the virtual apex 310 relative to the transducer array 112 and select a subset of the plurality of transducer elements 124 of the transducer array 112 as the active footprint 304. The active footprint 304 may define which of the digitized signals received by the transducer elements 124 of the transducer array 112 are to be processed by the beamformer processor 130.

For example, the beamformer processor 130 may be configured to perform filtering and/or decimation, to isolate and/or select the digitized signals corresponding to the relevant transducer elements 124 within the active footprint 304 aligned with the virtual apex 310 selected for beamforming. The beamformer processor 130 may define channels and/or time slots of the digitized data that correspond to the active footprint 304 with the virtual apex 310 that may be beamformed, with the remaining channels or time slots of digitized data (e.g., representing transducer elements 124 not within the active footprint 304) that may not be communicated for processing (e.g., discarded).

An elevation length 306 and an azimuth length of 308 of the sector FOV 302 are associated with an imaging angle of the sector FOV 302. The imaging angle may correspond to a three dimensional sweep angle centered at the virtual apex 310 defining a range along the azimuth and elevation planes 206, 208 from the active region 304 the controller circuit 136 can acquire ultrasound data of the region of interest. A size of the imaging angle and/or size of the sector FOV 302 may be defined by and/or based on a size of the active footprint 304. For example, the active footprint 304 may correspond to an array of 64 transducer elements 124 along the elevation plane 208 to define an elevation length 306 of the sector FOV 302, and 40 transducer elements 124 along the azimuth plane 206 to define an azimuth length of 308 of the sector FOV 302. Based on the active footprint 304, the sector FOV 302 may have the 3D imaging angle include 80 degrees along the azimuth plane 206 and 90 degrees along the elevation plane 208.

The controller circuit 136 may adjust a size of the imaging angle and/or the sector FOV 302 by adjusting the number of transducer elements 124 within the active footprint 304. For example, the controller circuit 136 may adjust the imaging angle to a 2D plane by adjusting the size of the active footprint to a single column of 40 transducer elements 124 along the azimuth plane 206.

In connection with FIGS. 4A-E, the controller circuit 136 is configured to independently control the transducer elements 124 used to acquire the ultrasound data of the region of interest from a sector FOV (e.g., sector FOV 410, 420, 430, 436, 440, 446, 450, 452) in at least one of an elevation direction (e.g., along the elevation plane 208) or the azimuth direction (e.g., along the azimuth plane 206). For example, the controller circuit 136 may adjust a position of the virtual apex (e.g., virtual apex 412, 432, 444, 456) and/or transducer elements 124 within an active footprint (e.g., active footprint 416, 426, 448) to adjust a position, imaging angle, and/or orientation of the sector FOV in the elevation and/or azimuth direction of the ultrasound probe 126.

Figure 4A:
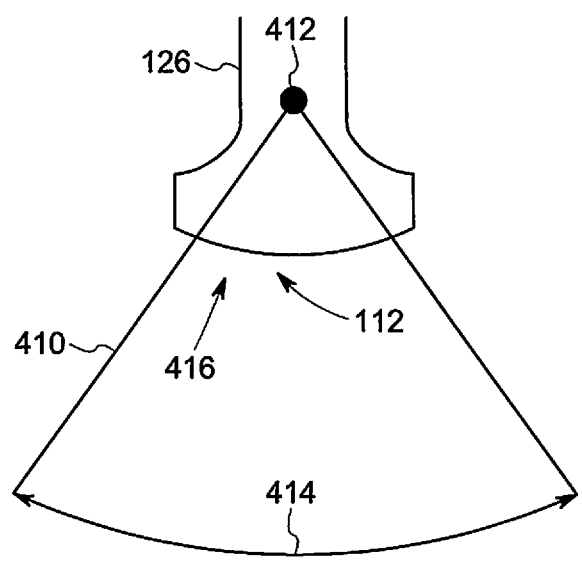
FIGS. 4A-E illustrate sector field of views of the ultrasound probe, in accordance with embodiments described herein.
Figure 4B:
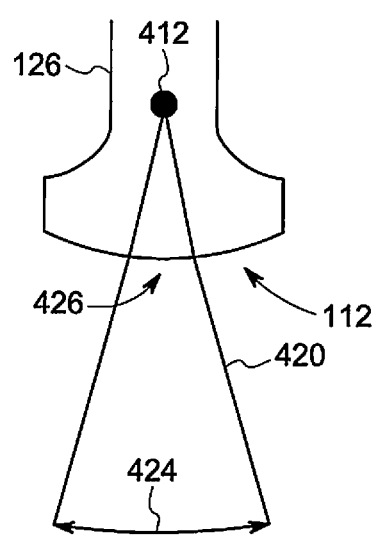
Figure 6A:
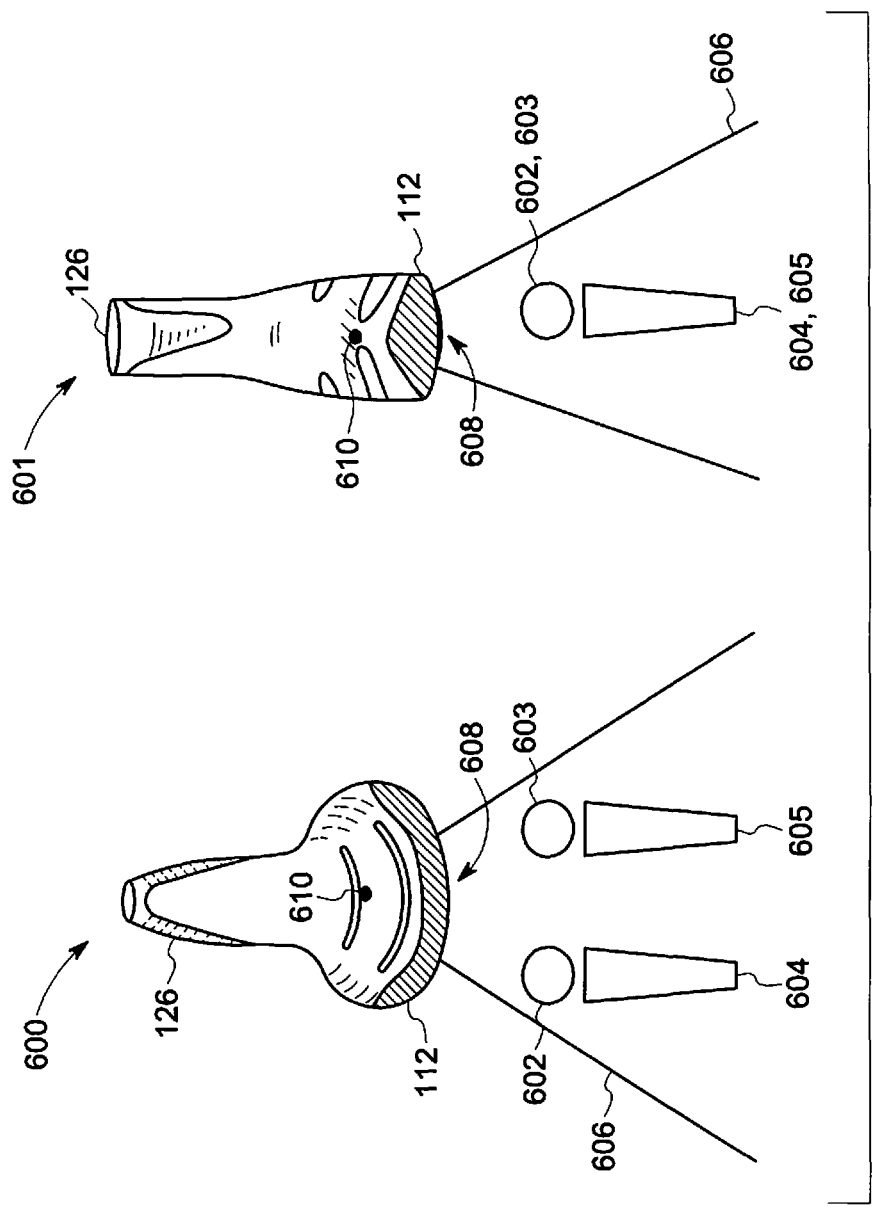
FIGS. 6A-C illustrate sector field of views of the ultrasound probe relative to at least one ultrasound obstructed regions, in accordance with an embodiment.
Figure 6B:
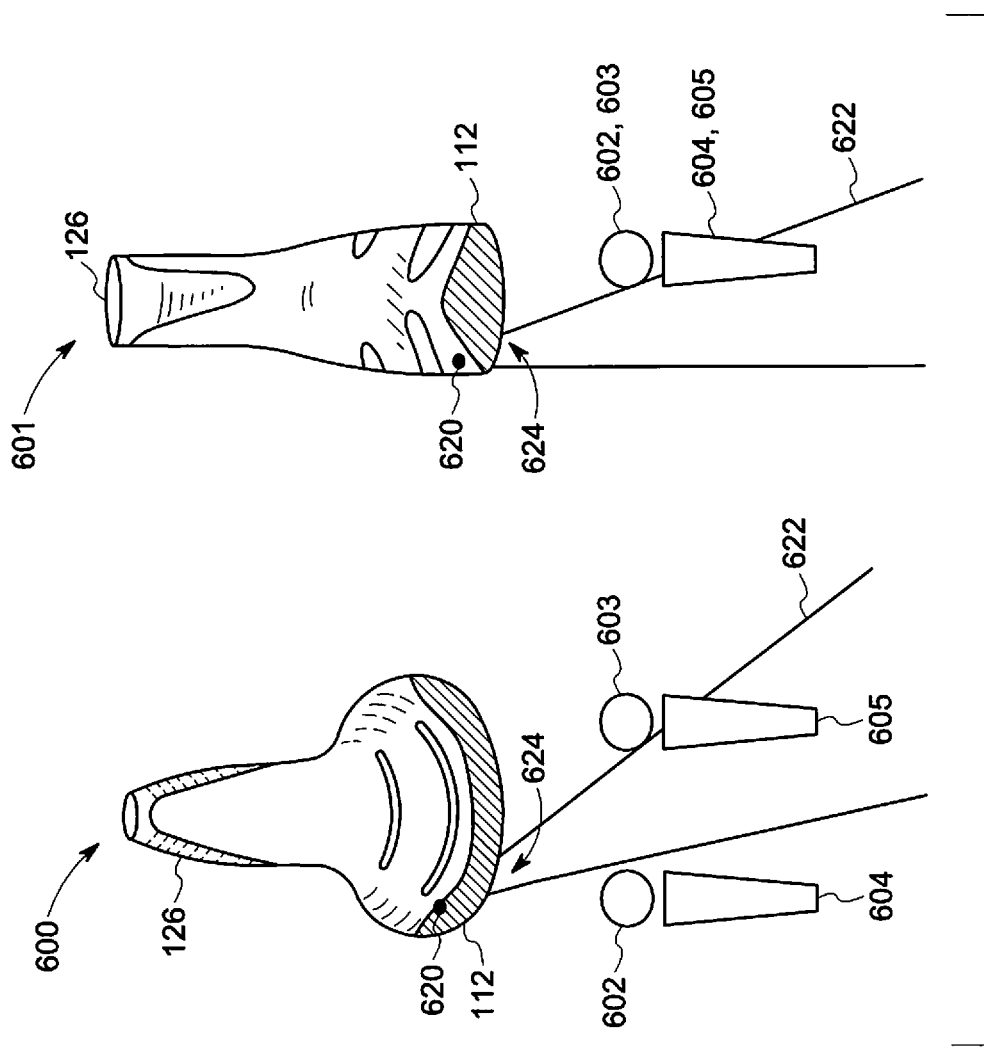

FIGS. 4A-E illustrate sector FOVs 410, 420, 430, 436, 440, 446, 450, 452 of the ultrasound probe 126, in accordance with embodiments described herein. The ultrasound probe 126 shown in FIGS. 4A-E is shown aligned along an azimuth plane (e.g., the azimuth plane 206). Each of the FIGS. 4A-B illustrates an adjustment of the sector FOVs 410, 420, 430, 436, 440, 446, 450, 452 by the controller circuit 136 by adjusting the virtual apex (e.g., the virtual apex 412, 432, 444, 456) and/or active footprint (e.g., active footprint 416, 426, 448) defining the sector FOV 410, 420, 430, 436, 440, 446, 450, 452. It may be noted that although FIGS. 4A-E illustrate changes in the sector FOVs 410, 420, 430, 436, 440, 446, 450, 452 along the azimuth plane, in various embodiments (e.g., as shown in FIGS. 6A-B) the sector FOV 410, 420, 430, 436, 440, 446, 450, 452 may be adjusted in three dimensions (3D) along the azimuth plane and/or elevation plane (e.g., the elevation plane 208).

The sector FOV 410 shown in FIG. 4A is formed at a virtual apex 412 extending from the transducer array 112, having an imaging angle 414. The sector FOV 410 includes an active footprint 416 of the transducer array 112. The active footprint 416 includes all of the transducer elements 124 of the transducer array 112. During the scan, the transducer elements 124 emit pulsed ultrasonic signals, at least a portion of the ultrasonic signals are reflected based from the ROI and received by the transducer elements 124. However, anatomical regions (e.g., bones, air pockets, and/or the like) within the ROI may obstruct and/or block the ultrasonic signals within the sector FOV 410. For example, the anatomical regions may create ultrasound obstructed regions formed by ultrasonic signals being blocked by anatomical regions. Based on a position of the anatomical regions the ultrasound obstructed regions are formed representing areas within the sector FOV 410 that ultrasound data is not acquired by the controller circuit 136. FIGS. 4B-4E represent adjustments to the sector FOV 410 by the controller circuit 136 to acquire ultrasound data that was not acquired based on the ultrasound obstructed regions.

The sector FOV 420 shown in FIG. 4B is formed at the virtual apex 412 extending from the transducer array 112 and an active footprint 426. The sector FOV 420 is shown having a reduced imaging angle 424 along the azimuth direction relative to the imaging angle 414 of the sector FOV 410. For example, to form the sector FOV 420 the controller circuit 136 reduced a number of transducer elements 124 that are included within the active footprint 426 relative to the active footprint 416 to form the imaging angle 424. Additionally or alternatively, the controller circuit 136 may increase the imaging angle 424 by increasing a number of transducer elements 124 in the active footprint 426. Optionally, as shown in FIG. 4C, the controller circuit 136 may adjust a position of the virtual apex (e.g., the virtual apex 412, 432) to adjust the imaging angle having the same active footprint 426.

Figure 4C:
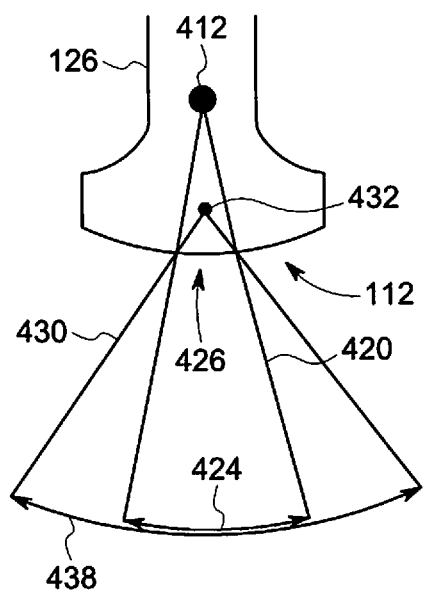

FIG. 4C shows the sector FOV 420 formed by the virtual apex 412 and the active footprint 426. The controller circuit 136 may adjust the imaging angle 424 along the azimuth direction of the sector FOV 420 to form the sector FOV 430 by adjusting a position of the virtual apex 412 while utilizing the same and/or similar active footprint 426. For example, the controller circuit 136 may adjust the virtual apex 412 towards the transducer array 112 to a position corresponding to the virtual apex 432. Based on the position of the virtual apex 432, the imaging angle 424 is increased and/or adjusted in the azimuth direction to form the imaging angle 438, which is larger relative to the imaging angle 424. It may be noted in various embodiments, the controller circuit 136 may adjust the imaging angle 424 along the elevation direction and/or the elevation direction and the azimuth direction.

Figure 4D:
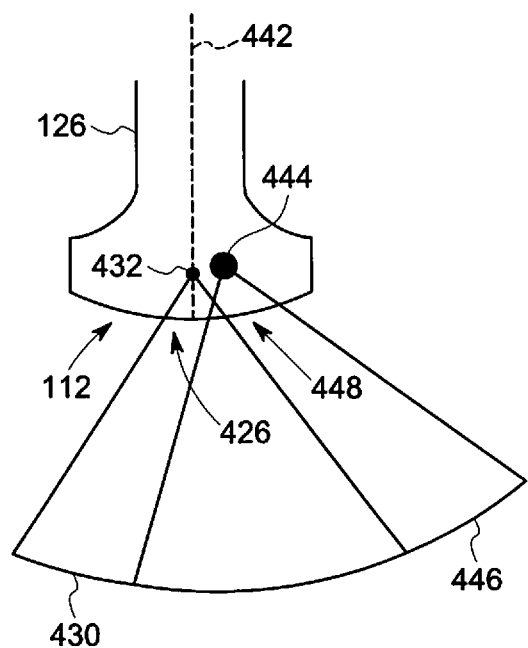

Additionally or alternatively, in connection with FIG. 4D, the controller circuit 136 may adjust an orientation of the sector FOV 430 by adjusting and/or shifting the virtual apex 432 from a symmetry axis 442 of the ultrasound probe 126. The symmetry axis 442 may traverse a middle position of the ultrasound probe 126. For example, the symmetry axis 442 may define opposing sides of the ultrasound probe 126 that are interposed by the symmetry axis 442. A position of the symmetry axis 442 may be configured such that the opposing sides are mirror images of each other. The virtual apex 432 and the active footprint 426 utilized to define the sector FOV 430 is positioned on the symmetry axis 442. The controller circuit 136 may adjust an orientation of the sector FOV 430 by shifting the sector FOV 430 along the azimuth direction to form the sector FOV 446. For example, the controller circuit 136 shifts the virtual apex 432 from the symmetry axis 442 to a position of the virtual apex 444, and shifts the active footprint 426 to the active footprint 448 such that at least a plurality of the transistor elements 124 in the active footprint 448 are not included in the active footprint 426. The sector FOV 446 is shifted with the virtual apex 448 such that the sector FOV 446 has a different orientation relative to the sector FOV 430.

Figure 4E:
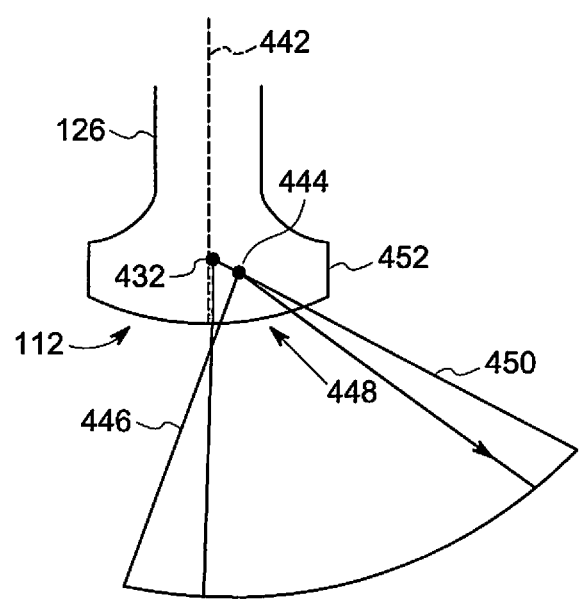

It may be noted, in connection with FIG. 4E, the orientation of the sector FOV 446 may be adjusted by shifting the virtual apex 432 utilizing the same active footprint 448. For example, the controller circuit 136 is configured to adjust the virtual apex 432 to the virtual apex 444 to form the sector FOV 450. The sector FOV 450 is tilted with respect to the sector FOV 446 towards an opposing end 452 of the ultrasound probe 126 along the azimuth direction.

Returning to FIG. 1, the beamformer processor 130 performs beamforming on the digitized signals of transducer elements along the sector FOV and outputs a radio frequency (RF) signal. The RF signal is then provided to an RF processor 132 that processes the RF signal. The RF processor 132 may include one or more processors. Optionally, the RF processor 132 may include a central controller circuit (CPU), one or more microprocessors, or any other electronic component capable of processing inputted data according to specific logical instructions. Additionally or alternatively, the RF processor 132 may execute instructions stored on a tangible and non-transitory computer readable medium (e.g., the memory 140). Optionally, the RF processor 132 may be integrated with and/or apart of the controller circuit 136. For example, the operations described being performed by the RF processor 132 may be configured to be performed by the controller circuit 136.

The RF processor 132 may generate different ultrasound image data types, e.g. B-mode, color Doppler (velocity/power/variance), tissue Doppler (velocity), and Doppler energy, for multiple scan planes or different scanning patterns. For example, the RF processor 132 may generate tissue Doppler data for multi-scan planes. The RF processor 132 gathers the information (e.g. I/Q, B-mode, color Doppler, tissue Doppler, and Doppler energy information) related to multiple data slices and stores the data information, which may include time stamp and orientation/rotation information, in the memory 140.

Alternatively, the RF processor 132 may include a complex demodulator (not shown) that demodulates the RF signal to form IQ data pairs representative of the echo signals. The RF or IQ signal data may then be provided directly to the memory 140 for storage (e.g., temporary storage). Optionally, the output of the beamformer processor 130 may be passed directly to the controller circuit 136.

The controller circuit 136 may be configured to process the acquired ultrasound data (e.g., RF signal data or IQ data pairs) and prepare and/or generate frames of ultrasound image data representing the ROI for display on the display 138. Optionally, the controller circuit 136 may combine and/or overlay a plurality of frames based on different sector FOVs to form a combined and/or filled ultrasound image data. Each of the frames utilized by the controller circuit 136 to form the combined and/or filled ultrasound image data includes ultrasound image data not included in the remaining frames. For example, the controller circuit 136 may generate a first frame for a sector FOV. The first frame may include a gap in ultrasound data representing a first obstructed ultrasound region. The controller circuit 136 may adjust the virtual apex and/or active footprint to form a second sector FOV. The controller circuit 136 may generate a second frame based on the second sector FOV that includes a gap in ultrasound data representing a second obstructed ultrasound region. The first obstructed ultrasound region is positioned at a different location within the ROI with respect to the second obstructed ultrasound region. For example, the first frame includes ultrasound image data not included in the second frame. The controller circuit 136 may overlay and/or fill the first frame with the second frame by including the ultrasound image data of the second frame representing the first obstructed ultrasound region to form the combined and/or filled ultrasound image data.

The controller circuit 136 may include one or more processors. Optionally, the controller circuit 136 may include a central controller circuit (CPU), one or more microprocessors, a graphics controller circuit (GPU), or any other electronic component capable of processing inputted data according to specific logical instructions. Having the controller circuit 136 that includes a GPU may be advantageous for computation-intensive operations, such as volume-rendering. Additionally or alternatively, the controller circuit 136 may execute instructions stored on a tangible and non-transitory computer readable medium (e.g., the memory 140).

The controller circuit 136 is configured to perform one or more processing operations according to a plurality of selectable ultrasound modalities on the acquired ultrasound data, adjust or define the ultrasonic pulses emitted from the transducer elements 124, adjust one or more image display settings of components (e.g., ultrasound images, interface components, positioning regions of interest) displayed on the display 138, and other operations as described herein. Acquired ultrasound data may be processed in real-time by the controller circuit 136 during a scanning or therapy session as the echo signals are received. Additionally or alternatively, the ultrasound data may be stored temporarily in the memory 140 during a scanning session and processed in less than real-time in a live or off-line operation.

The memory 140 may be used for storing processed frames of acquired ultrasound data that are not scheduled to be displayed immediately or to store post-processed images (e.g., shear-wave images, strain images), firmware or software corresponding to, for example, a graphical user interface, one or more default image display settings, programmed instructions (e.g., for the controller circuit 136, the beamformer processor 130, the RF processor 132), and/or the like. The memory 140 may be a tangible and non-transitory computer readable medium such as flash memory, RAM, ROM, EEPROM, and/or the like.

The memory 140 may store 3D ultrasound image data sets of the ultrasound data, where such 3D ultrasound image data sets are accessed to present 2D and 3D images. For example, a 3D ultrasound image data set may be mapped into the corresponding memory 140, as well as one or more reference planes. The processing of the ultrasound data, including the ultrasound image data sets, may be based in part on user inputs, for example, user selections received at the user interface 142.

The controller circuit 136 is operably coupled to a display 138 and a user interface 142. The display 138 may include one or more liquid crystal displays (e.g., light emitting diode (LED) backlight), organic light emitting diode (OLED) displays, plasma displays, CRT displays, and/or the like. The display 138 may display patient information, ultrasound images and/or videos, components of a display interface, one or more 2D, 3D, or 4D ultrasound image data sets from ultrasound data stored in the memory 140 or currently being acquired, measurements, diagnosis, treatment information, and/or the like received by the display 138 from the controller circuit 136.

The user interface 142 controls operations of the controller circuit 136 and is configured to receive inputs from the user. The user interface 142 may include a keyboard, a mouse, a touchpad, one or more physical buttons, and/or the like. Based on selections received by the user interface 142 the controller circuit 136 may adjust the sector FOV 302, 410, 420, 430, 446, 450 by shifting the virtual apex 310, 412, 432, 444, the active footprint 304, 416, 426, 448, and/or the imaging angle 414, 424, 438 of the ultrasound probe 126. Optionally, the display 138 may be a touchscreen display, which includes at least a portion of the user interface 142.

For example, a portion of the user interface 142 shown on a touchscreen display (e.g., the display 138) is configured to receive one or more selections associated and/or represented as a graphical user interface (GUI) generated by the controller circuit 136 shown on the display. The GUI may include one or more interface components that may be selected, manipulated, and/or activated by the user operating the user interface 142 (e.g., touchscreen, keyboard, mouse). For example, the controller circuit 136 is configured to adjust the sector FOV 302, 410, 420, 430, 446, 450 based on the selection of the one or more interface components of the GUI. The interface components may be presented in varying shapes and colors, such as a graphical or selectable icon, a slide bar, a cursor, and/or the like. Optionally, one or more interface components may include text or symbols, such as a drop-down menu, a toolbar, a menu bar, a title bar, a window (e.g., a pop-up window) and/or the like. Additionally or alternatively, one or more interface components may indicate areas within the GUI for entering or editing information (e.g., patient information, user information, diagnostic information), such as a text box, a text field, and/or the like.

In various embodiments, the interface components may perform various functions when selected, such as shifting the sector FOV 302, 410, 420, 430, 446, 450, adjusting the virtual apex 310, 412, 432, 444, adjusting the active footprint 304, 416, 426, 448, increasing and/or decreasing the imaging angle 414, 424, 438, selecting the scan being performed by the ultrasound imaging system 100, measurement functions, editing functions, database access/search functions, diagnostic functions, controlling acquisition settings, and/or system settings for the ultrasound imaging system 100 performed by the controller circuit 136.

Figure 5:
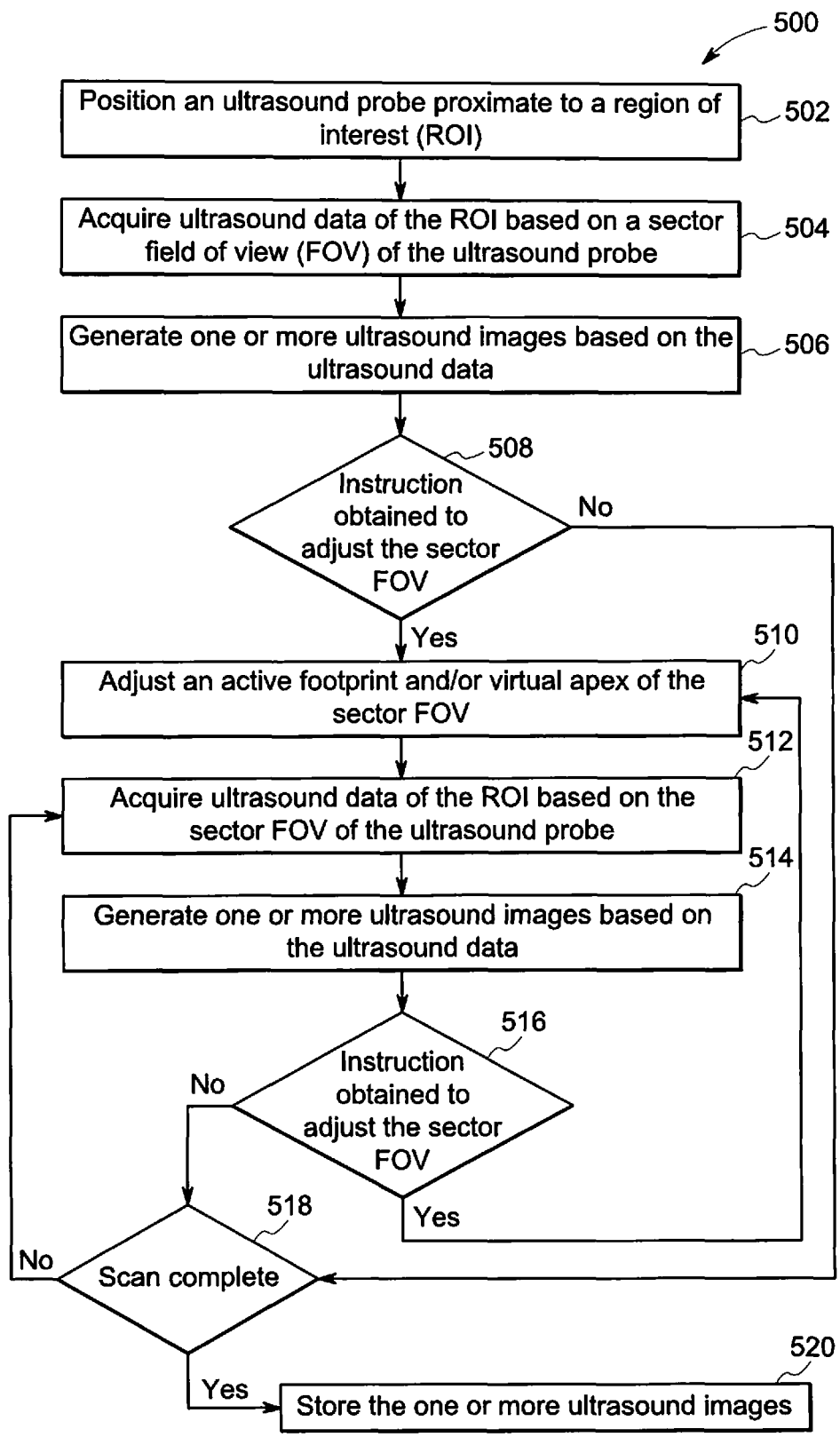
FIG. 5 is a flow chart of a method in accordance with an embodiment.

FIG. 5 is a flow chart of a method 500 in accordance with an embodiment. The method 500 may be, for example, adjusting a sector FOV of the ultrasound probe 126 during a scan of the ultrasound imaging system 100. The method 500 may employ structures or aspects of various embodiments (e.g., the controller circuit 136, the ultrasound probe 126, the ultrasound imaging system 100, and/or the like) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

Beginning at 502, the ultrasound probe 126 is positioned proximate to a region of interest (ROI). The ROI (e.g., heart, left ventricular outflow tract, breast tissues, liver tissues, cardiac tissues, prostate tissues, neonatal brain, embryo, abdomen, and the like) may be based on the scan being performed by the ultrasound imaging system 100. The scan may be a neonatal brain scan, a gynecological exam, abdominal scan, a guided biopsy, an embryonic scan, and/or the like. For example, the user may select a scan utilizing the user interface 142 from a GUI displayed on the display 138. The controller circuit 136 may receive a selection of the scan and adjust the acquisition settings (e.g., an amplitude, pulse width, frequency, and/or the like) of the ultrasound probe 126 based on the selected scan. When the ultrasound probe 126 is positioned at a scanning location proximate to the ROI, the controller circuit 136 may receive a selection from the user interface 142 indicating the ultrasound probe 126 is positioned proximate to the ROI. For example, the user may position the transducer array 112 of the ultrasound probe 126 against a skin of the patient at a location proximate to the ROI. Optionally, the controller circuit 136 may receive a trigger, such as a selection of the user interface component 210 and/or a user interface 142 to initiate the scan and/or instructing the controller circuit 136 that the ultrasound probe 126 is positioned proximate to the ROI.

At 504, the controller circuit 136 acquires ultrasound data of the ROI based on a sector FOV of the ultrasound probe 126. For example, in connection with FIG. 6A, the controller circuit 136 is configured to control the ultrasound probe 126 to acquire ultrasound data from a sector FOV 606 utilizing the transducer elements 124 of the transducer array 112 within an active footprint 608 at a virtual apex 610.

FIG. 6A illustrates the sector FOV 606 of the ultrasound probe 126 relative to at least one ultrasound obstructed regions 604, 605, in accordance with an embodiment. The ultrasound probe 126 is shown in FIG. 6A in two different views 600, 601. For example, the ultrasound probe 126 is shown in an azimuth view 600 having the ultrasound probe 126 aligned along an azimuth plane (e.g., the azimuth plane 206), and in an elevation view 600 having the ultrasound probe 126 aligned along an elevation plane (e.g., the elevation plane 208). The transducer elements 124 may emit pulsed ultrasonic signals, at least a portion of the ultrasonic signals are reflected based from the ROI and received by the transducer elements 124. Based on the active footprint 608 and the virtual apex 610, the beamformer processor 130 may isolate and/or select the digitized signals corresponding to the ultrasonic signals received by the transducer elements 125 of the active footprint 608 along the virtual apex 610.

The ultrasound obstructed regions 604, 605 are the result of ultrasonic signals begin blocked by anatomical regions 602, 603. For example, the anatomical regions 602, 603 may represent bones, air pockets, and/or the like within the ROI that reflect ultrasonic signals emitted by the transducer elements 124. Based on a position of the anatomical regions 602, 603, the ultrasound obstructed regions 604, 605 are formed representing areas within the sector FOV 606 that does not include ultrasound data.

At 506, the controller circuit 136 generates one or more ultrasound images based on the ultrasound data. For example, the beamformer processor 130 is configured to perform the beamforming on the selected digitized signals based on the sector FOV 606 and output a RF signal. Based on the RF signal, the controller circuit 136 may generate one or more ultrasound images, which are shown on the display 138.

At 508, the controller circuit 136 determines whether instructions are obtained to adjust the sector FOV 606. For example, the controller circuit 136 may detect a selection of the one or more user interface components 210 of the ultrasound probe 126 representing instructions to adjust the sector FOV 606. Additionally or alternatively, the controller circuit 126 may detect a selection of one or more user selections of a user interface 142 based on a GUI shown on the display 138 representing instructions to adjust the sector FOV 606.

If the controller circuit 136 determines the instructions were obtained, at 510, the controller circuit 136 adjusts the active footprint 608 and/or virtual apex 610 of the sector FOV 606. For example, in connection with FIG. 6B, the controller circuit 136 may adjust the sector FOV 606 based on at least one of the ultrasound obstructed regions 604, 605.

FIG. 6B illustrates a sector FOV 622 of the ultrasound probe 126 relative to the at least one ultrasound obstructed regions 604, 605, in accordance with an embodiment. The controller circuit 136 may shift the virtual apex 610 and the corresponding sector FOV 606 to form the sector FOV 622 based on the instructions received from the one or more user interface components 210 and/or the user interface 142. For example, the controller circuit 136 may shift the virtual apex 610 to a virtual apex 620 to form the sector FOV 622. The sector FOV 622 also includes a different active footprint 624 that is shifted from the active footprint 608 by the controller circuit 136 to not include transducer elements 124 in the azimuth direction and the elevation direction. It may be noted based on the shift in the virtual apex 620 the sector FOV 622 has a different orientation relative to the sector FOV 606. For example, the sector FOV 622 is configured by the controller circuit 136 to encompass the ultrasound obstructed region 605 that was previously blocked by the anatomical region 603.

Returning to FIG. 5, at 512, the controller circuit 136 acquires ultrasound data of the ROI based on the sector FOV 622 of the ultrasound probe 126. For example, the transducer elements 124 may emit pulsed ultrasonic signals, at least a portion of the ultrasonic signals are reflected based from the ROI and received by the transducer elements 124. Based on the active footprint 624 and the virtual apex 620, the beamformer processor 130 may isolate and/or select the digitized signals corresponding to the ultrasonic signals received by the transducer elements 125 of the active footprint 608 along the virtual apex 620.

It may be noted, based on the change in orientation of the sector FOV 622 relative to the sector FOV 606, the controller circuit 126 may acquire ultrasound data of the ROI that includes the obstructed ultrasound region 605 that was not acquire using the sector FOV 606. For example, the controller circuit 136 acquires additional ultrasound data based on the shifted sector FOV 622 that was not obtained with the prior sector FOV 606

At 514, the controller circuit 136 generates one or more ultrasound images based on the ultrasound data. For example, the beamformer processor 130 is configured to perform the beamforming on the selected digitized signals based on the sector FOV 622 and output a RF signal. Based on the RF signal, the controller circuit 136 may generate one or more ultrasound images, which are shown on the display 138. Additionally or alternatively, the controller circuit 136 may overlay and/or superimpose portions of the one or more ultrasound images acquired using the sector FOV 622 corresponding to the obstructed ultrasound region 605 to the one or more ultrasound images based on the ultrasound data acquired using the sector FOV 606.

At 516, the controller circuit 136 determines whether instructions are obtained to adjust the sector FOV. For example, the controller circuit 136 may detect a selection of the one or more user interface components 210 of the ultrasound probe 126 representing instructions to adjust the sector FOV 606. Additionally or alternatively, the controller circuit 136 may detect a selection of one or more user selections of a user interface 142 based on a GUI shown on the display 138 representing instructions to adjust the sector FOV 606.

If the controller circuit 136 determines the instructions were obtained, returning to 516, the controller circuit 136 adjusts the active footprint 624 and/or virtual apex 620 of the sector FOV 622. For example, in connection with FIG. 6C, the controller circuit 136 may adjust the sector FOV 622 based on at least one of the ultrasound obstructed regions 604, 605.

Figure 6C:
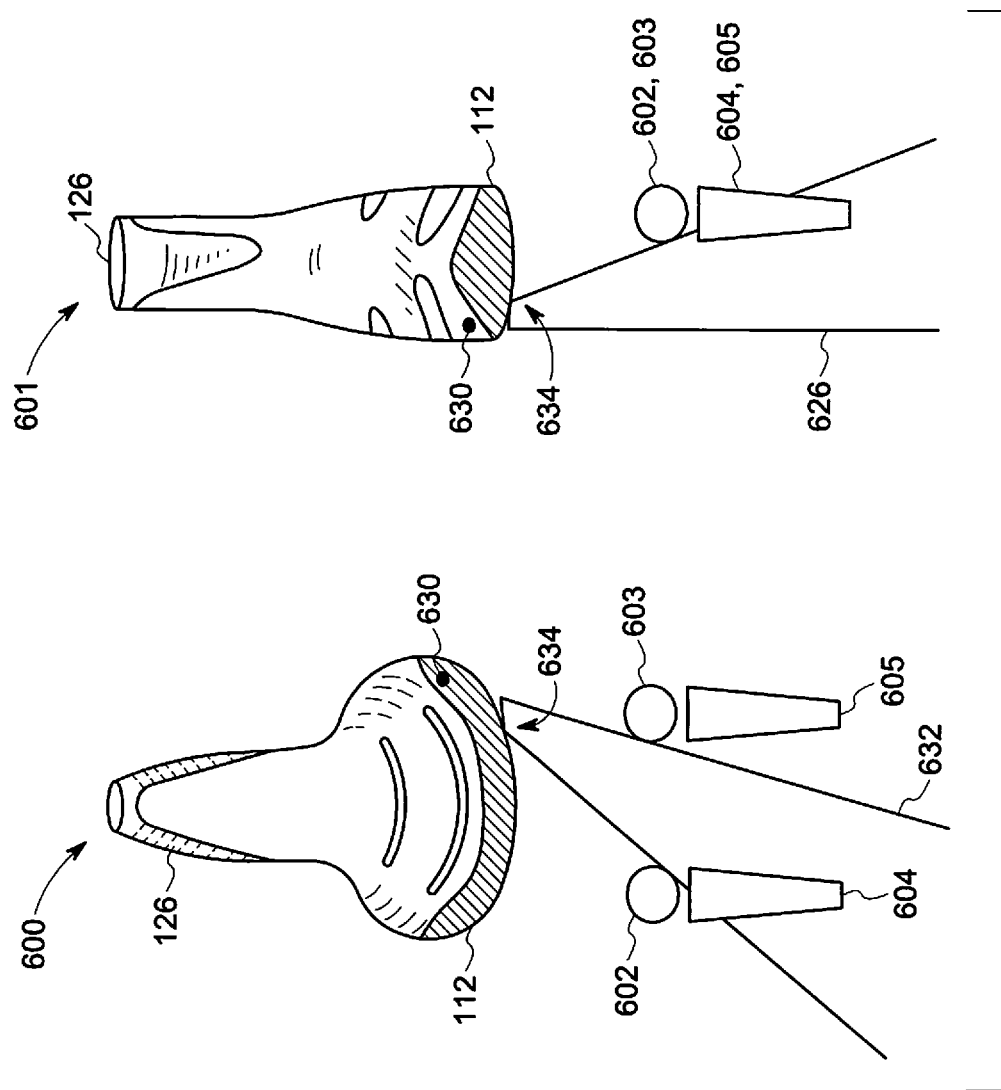

FIG. 6C illustrates a sector FOV 632 of the ultrasound probe 126 relative to the at least one ultrasound obstructed regions 604, 605, in accordance with an embodiment. The controller circuit 136 may shift the virtual apex 620 and the corresponding sector FOV 622 to form the sector FOV 632 based on the instructions received from the one or more user interface components 210 and/or the user interface 142. For example, the controller circuit 136 may shift the virtual apex 620 to a virtual apex 630 to form the sector FOV 632. The sector FOV 632 also includes a different active footprint 634 that is shifted from the active footprint 624 by the controller circuit 136 to not include transducer elements 124 in the azimuth direction. For example, the controller circuit shifts the sector FOV 622 to form the sector FOV 632 such that the sector FOV 622 includes a first segment or portion of the transducer elements 124 corresponding to the active footprint 624 and the sector FOV 632 includes a second segment or portion of the transducer elements 124 corresponding to the active footprint 634. Optionally, the first segment (e.g., the active footprint 624) does not include a portion of the second segment (e.g., the active footprint 634). It may be noted based on the shift in the virtual apex 630 the sector FOV 632 has a different orientation relative to the sector FOV 622. For example, the sector FOV 632 is configured by the controller circuit 136 to encompass the ultrasound obstructed region 604.

It may be noted, based on the change in orientation of the sector FOV 632 relative to the sector FOV 632, the controller circuit 136 may acquire ultrasound data of the ROI that includes the obstructed ultrasound region 604 that was not acquire using the sector FOVs 606, 622. For example, the controller circuit 136 acquires additional ultrasound data based on the shifted sector FOV 632 that was not obtained with the prior sector FOVs 606 and 622.

Returning to FIG. 5, if the controller circuit 136 determines that the instructions were not obtained, at 518, the controller circuit 136 determines whether the scan is complete. For example, the controller circuit 136 may detect a selection of the one or more user interface components 210 of the ultrasound probe 126 representing instructions that the scan is complete. Additionally or alternatively, the controller circuit 136 may detect a selection of one or more user selections of a user interface 142 based on a GUI shown on the display 138 representing instructions that the scan is complete.

If the scan is complete, at 520 the controller circuit 136 may store the one or more ultrasound images obtained during the scan. For example, the controller circuit 136 may store the one or more ultrasound images on the memory 104 and/or to a remote system (e.g., image server).

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An ultrasound imaging system comprising:
   a matrix array probe including an aperture comprising a plurality of transducer elements arranged in an array, wherein the plurality of transducer elements form a curved surface of the matrix array probe that varies along an elevation direction and an azimuth direction; and
   a controller circuit configured to control the matrix array probe to acquire ultrasound data from a first position of a virtual apex relative to the curved surface defining a first sector field of view (FOV) with a first contiguous subset of the plurality of transducer elements, and, based on detecting at least one ultrasound obstructed region in the first FOV, shift the virtual apex to a second position relative to the curved surface defining a second sector FOV with a second contiguous subset of the plurality of transducer elements, wherein the second position of the virtual apex is different from the first position in at least one of the elevation direction and the azimuth direction of the curved surface and wherein the second position encompasses the ultrasound obstructed region.

2. The ultrasound imaging system of claim 1, wherein the controller circuit is configured to adjust an imaging angle of the first sector FOV by adjusting a number of the plurality of transducer elements of the first subset of the plurality of transducer elements.

3. The ultrasound imaging system of claim 2, wherein the imaging angle is adjusted along at least one of the azimuth direction or the elevation direction.

4. The ultrasound imaging system of claim 1, wherein the at least one ultrasound obstructed region is formed by an anatomical region, the anatomical region including at least one of an air pocket or bone within the first FOV that reflects ultrasonic signals emitted by the first subset of the plurality of transducer elements.

5. The ultrasound imaging system of claim 1, wherein the controller circuit is configured to independently control each transducer element of a select contiguous subset of the plurality of transducer elements used to acquire the ultrasound data from a select sector FOV.

6. The ultrasound imaging system of claim 1, wherein the matrix array probe includes a housing having one or more user interface components, and wherein the controller circuit is configured to adjust a select sector FOV based on a selection of the one or more user interface components.

7. The ultrasound imaging system of claim 1, further comprising a touchscreen display communicatively coupled to the controller circuit, wherein the touchscreen display is configured to receive one or more user selections, the controller circuit is configured to adjust a select sector FOV based on the one or more user selections.

8. The ultrasound imaging system of claim 1, wherein the first subset of the plurality of transducer elements does not include a portion of the second subset of the plurality of transducer elements.

9. The ultrasound imaging system of claim 1, wherein the virtual apex is shifted from a symmetry axis of the matrix array probe.

10. A method for adjusting a sector field of view (FOV) of a matrix array probe, comprising:
    acquiring ultrasound data from a matrix array probe including an aperture comprising a plurality of transducer elements arranged in an array, wherein the plurality of transducer elements form a curved surface of the matrix array probe that varies along an elevation direction and an azimuth direction, wherein the ultrasound data is acquired from a first position of a virtual apex defining a first sector field of view (FOV with a first contiguous subset of the plurality of transducer elements; and
    based on detecting at least one ultrasound obstructed region in the first FOV, shifting the virtual apex to a second position defining a second sector FOV with a second contiguous subset of the plurality of transducer elements, wherein the second position of the virtual apex is different from the first position in at least one of the elevation direction and the azimuth direction of the curved surface.

11. The method of claim 10, wherein the second position of the virtual apex encompasses the at least one ultrasound obstructed region.

12. The method of claim 11, wherein the at least one ultrasound obstructed region is formed by an anatomical region, the anatomical region including at least one of an air pocket or bone within the first FOV that reflects ultrasonic signals emitted by the first subset of the plurality of transducer elements.

13. The method of claim 10, further comprising receiving a user input indicative of an amount to shift the virtual apex, wherein during the shifting operation the virtual apex is shifted by the amount.

14. The method of claim 10, wherein shifting includes adjusting a select sector FOV by adjusting an imaging angle of the sector FOV in at least one of the elevation direction or the azimuth direction.

15. The method of claim 10, wherein the first sector FOV includes a first segment of the at least one ultrasound obstructed region and the second sector FOV includes a second segment of the at least one ultrasound obstructed region.

16. The method of claim 10, wherein shifting includes shifting the virtual apex is shifted from a symmetry axis of the matrix array probe.

17. An ultrasound imaging system comprising:
    a matrix array probe including an aperture comprising a plurality of transducer elements arranged in an array, wherein the plurality of transducer elements form a curved surface of the matrix array probe that varies along an elevation direction and an azimuth direction, wherein the plurality of transducer elements form a curved surface area of the matrix array probe; and
    a controller circuit configured to control the matrix array probe to acquire ultrasound data with respect to a first position of a virtual apex defining a first sector field of view (FOV) with a first contiguous subset of the plurality of transducer elements, wherein the controller circuit is further configured to shift the virtual apex from the first position to a second position defining a second sector FOV with a second contiguous subset of the plurality of transducer elements based on detecting at least one ultrasound obstructed region in the first FOV, wherein the second position of the virtual apex is different from the first position in at least one of the elevation direction and the azimuth direction of the curved surface, and wherein at least a portion of the second subset of transducer elements is different from the first subset.

18. The ultrasound imaging system of claim 17, wherein the virtual apex is shifted from a symmetry axis of the matrix array probe.

19. The ultrasound imaging system of claim 17, wherein the second subset of the transducer elements encompasses the at least one ultrasound obstructed region.

20. The ultrasound imaging system of claim 17, wherein the first sector FOV includes a first segment of the at least one ultrasound obstructed region and the second sector FOV includes a second segment of the at least one ultrasound obstructed region.

* * * * *